United States Patent [19]

Hanna, Jr. et al.

[11] Patent Number: 5,348,880
[45] Date of Patent: * Sep. 20, 1994

[54] TUMOR ASSOCIATED MONOCLONAL ANTIBODY 81AV/78

[75] Inventors: Michael G. Hanna, Jr., Frederick; Martin V. Haspel, Silver Spring, both of Md.; Herbert C. Hoover, Jr., Hingham, Mass.

[73] Assignee: Akzo N.V., Arnhem, Netherlands

[*] Notice: The portion of the term of this patent subsequent to May 9, 2006 has been disclaimed.

[21] Appl. No.: 94,589

[22] Filed: Jul. 20, 1993

Related U.S. Application Data

[63] Continuation of Ser. No. 701,281, May 16, 1991, abandoned, which is a continuation-in-part of Ser. No. 636,179, Dec. 31, 1990, abandoned, which is a continuation-in-part of Ser. No. 302,155, Jan. 25, 1989, Pat. No. 5,106,738, which is a continuation-in-part of Ser. No. 697,078, Jan. 31, 1985, Pat. No. 4,828,991, which is a continuation-in-part of Ser. No. 575,533, Jan. 31, 1984, abandoned.

[51] Int. Cl.$^5$ .................... C12N 5/22; C07K 15/28
[52] U.S. Cl. ........................... 435/240.27; 530/388.8
[58] Field of Search ................. 530/388.8; 435/240.27

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 435/2 |
| 4,340,586 | 7/1982 | Ehrlich et al. | 424/85 |
| 4,355,023 | 10/1982 | Bekierkunst et al. | 424/92 |
| 4,471,057 | 9/1984 | Koprowski et al. | 436/518 |
| 4,522,918 | 6/1985 | Schlom | 435/68 |
| 4,612,282 | 9/1986 | Schlom et al. | 435/68 |
| 4,613,576 | 9/1986 | Cote et al. | 436/548 |
| 4,618,577 | 10/1986 | Handley et al. | 435/7 |
| 4,661,586 | 4/1987 | Levy et al. | 530/387 |
| 4,828,991 | 5/1989 | Hanna et al. | 435/68 |
| 4,997,762 | 3/1991 | Hanna et al. | 435/240.27 |

FOREIGN PATENT DOCUMENTS 793000415 1/1978 European Pat. Off. .

OTHER PUBLICATIONS

Jean L. Marx, "Monoclonal Antibodies in Cancer," *Science*, vol. 216 (1982), pp. 283–285.

R. K. Oldman and R. V. Smalley, "Immunotherapy: The Old and the New," *J. Biol. Response Modifiers*, vol. 2 (1983), pp. 1–37.

R. Levy et al., *Annual Review of Medicine*, vol. 34, pp. 107–116 (1983).

M. Herlyn et al., *Proc. Natl. Acad. Sci.*, USA, vol. 76(3), pp. 1438–1442 (Mar. 1979).

M. Herlyn et al., *J. Clinical Immunology*, vol. 2(2), pp. 135–140 (1982).

Paul T. Stratte et al., "In Vivo Effects of Murine Monoclonal Anti-Human T Cell Antibodies in Subhuman Primates," *J. Biol. Response Modifiers*, vol. 1 (1982), pp. 137–148.

R. J. Cote et al., "Generation of Human Monoclonal Antibodies Reactive with Cellular Antigens," *Proc. Natl. Acad. Sci.*, vol. 80 (Apr. 1983), pp. 2026–2030.

H. C. Hoover, Jr. et al., "Delayed Cutaneous Hypersensitivity to Autologous Tumor Cells in Colorectal Cancer Patients Immunized with an Autologous Tumor Cell: Bacillus Calmette–Guerin Vaccine," *Cancer Research*, vol. 44 (Apr. 1984), pp. 1671–1676.

L. C. Peters et al., "Preparation of Immunotherapeutic Autologous Tumor Cell Vaccines from Solid Tumors," *Cancer Research*, vol. 39 (Apr. 1979), pp. 1353–1360.

(List continued on next page.)

*Primary Examiner*—David L. Lacey
*Assistant Examiner*—Susan A. Loring
*Attorney, Agent, or Firm*—William M. Blackstone

[57] ABSTRACT

This invention relates to human monoclonal antibody 81AV78 produced by a transformed B-cell line, having ATCC accession number CRL 10750 derived from B-cells of cancer patients actively immunized with autologous tumor antimen. This monoclonal antibody can be used in both diagnostic procedures and therapy for human cancers.

2 Claims, No Drawings

OTHER PUBLICATIONS

L. Lindholm et al., "Monoclonal Antibodies against Gastrointestinal Tumour-Associated Antigens Isolated as Monosialogangliosides," *Int. Arch. Allergy Appl. Immuno.*, vol. 71 (1983), pp. 178–181.

H. Koprowski et al., *Somat. Cell Genet.*, vol. 5 (1979), pp. 957–972.

L. Ollson and H. S. Kaplan, "Human-human Hybridomas producing Monoclonal Antibodies of Predefined Antigenic Specificity," *Proc. Natl. Acad. Sci.*, vol. 77, pp. 5429–5431.

J. L. Butler et al., "Delineation of Optimal Conditions for Producing Mouse-Human Heterohybridomas from Human Peripheral Blood B Cells of Immunized Subjects" *J. Immunology*, vol. 130, No. 1, pp. 165–168.

*Frederick Cancer Research Center Annual Report*, 1980, "Immunotherapy," pp. 64–65.

M. Herlyn et al., *Int. J. Cancer*, vol. 27, pp. 769–774 (1981).

Z. Steplewski et al., *Cancer Research*, vol. 41, pp. 2723–2727 (Jul., 1981).

*Stedman's Medical Dictionary*, 24th Ed., Williams & Wilkins, Baltimore, Md., (1982), p. 144.

*Handbook of Monoclonal Antibodies*, A. Ferrone et al., Eds. Noyes Pub. (1985), pp. 304–346.

*Monoclonal Antibodies in Clinical Medicine*, A. J. McMichael et al., Ed., Academic Press, London (1982), pp. 111–128, E. S. Lennox et al.

*Monoclonal Antibodies in Clinical Medicine*, A. J. McMichael et al., Ed., Academic Press, London (1982), pp. 17–35, Kaplan et al.

*Monoclonal Antibodies and Cancer*, B. D. Boss et al., Eds., Academic Press, Orlando (1983), pp. 163–170, M. C. Glassy et al.

*Monoclonal Antibodies and Cancer*, B. D. Boss et al., Eds., Academic Press, Orlando (1983), pp. 171–180, K. Sikora et al.

*Monoclonal Antibodies and Cancer*, B. D. Boss et al., Eds., Academic Press, Orlando 91983), pp. 135–142, N. N. H. Teng et al.

*Monoclonal Antibodies and Cancer*, B. D. Boss et al., Eds., Academic Press, Orlando (1983), pp. 143–155, K. A. Foon et al.

*Monoclonal Antibodies and Cancer*, B. D. Boss et al., Eds., Academic Press, Orlando (1983), pp. 181–184, P. A. W. Edwards et al.

D. Kozbor et al., *Proc. Natl. Acad. Sci.*, vol. 79, pp. 6651–6655 (1982).

T. Takayama, *Nihon. Univ. J. Med.*, vol. 26, No. 5, Abstract, (1984).

J. E. Boyd et al., *Trends in Biotechnology*, vol. 2, No. 3, pp. 70–77, (1984).

D. L. Toffaletti et al., *J. Immunology*, vol. 130, No. 6, pp. 2982–2986 (1983).

R. W. O'Donnell et al., *Som. Cell Mol. Gen.*, vol. 10, No. 2, pp. 195–204 (1984).

Haspel et al., *Cancer Research*, vol. 45, pp. 3951–3961 (Aug. 1985).

Finan et al., *Br. J. Cancer*, vol. 46, No. 1, Abstract (1982).

Sikora et al., *Br. J. Cancer*, vol. 43, No. 5, pp. 696–700.

Sikora et al., *Nature*, vol. 300, pp. 316–317.

Wunderlich et al., *Eur. J. Cancer Clin. Oncol.*, vol. 17, No. 7, pp. 719–730.

J. Schlom et al., *Prac. Natl. Acad. Sci., USA*, vol. 77, No. 11, pp. 6841–6845 (Nov., 1980).

Kohler et al., *Nature*, vol. 256, pp. 495–498 (Aug. 1975).

Liao et al., *Cancer Research*, vol. 38, No. 12, pp. 4395–4400 (1978).

Schlom, et al., Cancer Imaging with Radiolabeled Antibodies, ed. by David M. Goldenberg, p. 313–335, 1990.

McCabe, et al., Cancer Research, vol. 48:4348–4353, Aug. 1, 1988.

TUMOR ASSOCIATED MONOCLONAL ANTIBODY 81AV/78

This application is a continuation of U.S. patent application Ser. No. 07/701,281, filed May 16, 1991, now abandoned, which is a continuation-in-part of U.S. patent application Ser. No. 07/636,179, filed Dec. 31, 1990, now abandoned, which is a continuation-in-part of U.S. patent application Ser. No. 07/302,155, filed Jan. 25, 1989, issued as U.S. Pat. No. 5,106,738 on Apr. 21, 1992, which is continuation-in-part of U.S. patent application Ser. No. 06/697,078, filed Jan. 31, 1985, issued as U.S. Pat. No. 4,828,991 on May 9, 1989, which itself is a continuation-in-part of U.S. patent application Ser. No. 067,575,533, filed Jan. 31, 1984, now abandoned.

DESCRIPTION OF THE INVENTION

This invention relates to monoclonal antibodies produced by transformed B-cell lines derived from B-cells of cancer patients actively immunized with autologous tumor antigen. These monoclonal antibodies can be used in both diagnostic procedures and therapy for human cancers. This invention also relates to diagnostic procedures and therapeutic approaches using these monoclonal antibodies.

BACKGROUND OF THE INVENTION

Currently available treatments for cancer, particularly radiation therapy and chemotherapy, are based upon the rationale that cancer cells are relatively more sensitive to these treatments than normal cells. However, severe toxicity for normal tissues imposes major limitations to these therapies. In contrast, antibody molecules exhibit exquisite specificity for their antigens. Researchers have therefore sought to isolate antibodies specific for cancer cells as the "long-sought 'magic bullet' for cancer therapy" (*Science*, 1982, 216:283).

Antibodies are protein molecules normally synthesized by the B-cell lymphocytes produced by bone marrow and carried in the blood stream. For any antigen entering the body, i.e., any foreign molecule from a simple organic chemical to a complex protein, antibodies are produced which recognize and attach to that particular chemical structure. The unique chemical structure on the antigen to which a particular antibody can bind is referred to as an antigenic determinant or epitope. B-cell lymphocytes in the body, referred to as B-cells, lymphocytes, or leukocytes, exist as hundreds of millions of different genetically programmed cells, each producing an antibody specific for a different determinant. An antigen, which stimulates antibody production, can have several determinants on its surface. On encountering an antigen, a B-cell carrying on its surface an antibody specific for a determinant on that antigen will replicate. This clonal expansion results in many daughter cells that secrete that antibody into the blood stream.

Because of the specificity of antibodies in recognizing and binding to antigens, it was desired to produce antibodies in quantity that are specific for a single determinant, thus binding only to antigens or tissues having that particular determinant.

B-cells do not grow in a continuous culture unless they have been altered by hybridization with an "immortal" cell or by being transformed with either viral or tumor DNA. When cultured, hybridomas and transformed cells produce antibodies specific for a single determinant on a particular antigen. Such antibodies are referred to as "monoclonal antibodies."

Monoclonal antibodies are produced by B-lymphocyte cell lines that have been transformed, either spontaneously or intentionally, with a lymphotropic virus such as Epstein-Barr Virus (EBV). Transformation can also be accomplished using other transforming agents, such as viral DNA and cellular DNA. These cells, unlike hybridoma cells, possess a normal human diploid number (46) of chromosomes.

Monoclonal antibodies are synthesized in pure form uncontaminated by other immunoglobulins. With monoclonal antibody producing cells it is possible to produce virtually unlimited quantities of an antibody that is specific for one determinant on a particular antigen.

It has been believed that if antibodies specific for particular cancer cells were available, they could be used in various methods of treatment and diagnosis. Some antibodies could inactivate or kill particular tumor cells merely by attaching to the cell at the determinant for which they are specific. Other antibodies may bind to the surface of effector lymphocytes or macrophages, converting them into tumor antigen-specific killer cells.

Monoclonal antibodies can also increase the specificity of chemotherapeutic drugs, toxins and radioactive isotopes, thus increasing their efficacy while decreasing their toxicity by being conjugated to them. In addition, antibodies conjugated with radionuclides or metallic tracers can be used for imaging for in vivo diagnosis and localization of metastases. The antibodies can also be used for detecting the presence of tumor antigens in blood, as a diagnostic and/or prognostic test for cancer. Also, monoclonal antibodies can be used to isolate tumor antigens for potential use in a standardized vaccine.

DESCRIPTION OF THE PRIOR ART

Past attempts at deriving monoclonal antibodies specific for human cancers have taken two routes with respect to B-cells: 1) B-cells have been extracted from spleens of mice that were immunized against human tumors, U.S. Pat. 4,172,124; and 2) human B-cells have been extracted from either peripheral blood or from lymph nodes draining tumors in cancer patients. Neither approach has yielded satisfactory results.

Mice immunized against human tumors have too broad a reactivity. That is, most of the mouse monoclonal antibodies generated react with human antigens present on normal as well as on tumor tissue. An antibody that reacts only with tumor cells is very difficult to select from among the large variety of antibodies produced. For example, 20,000 hybridomas derived from mice immunized with human small-cell lung carcinoma were screened for reactivity with tumor cells (*Science*, 1982, 216:283). In contrast to a very low frequency ($<0.4\%$) observed by this research group, the method used to obtain the present antibodies results in up to 16% of the hybridomas derived from immunized colon patients producing monoclonal antibodies that react specifically with tumor cells. In addition, monoclonal antibodies derived from mouse B-cells have limited potential for application in cancer therapy. After repeated administration they stimulate the human immune system to produce "anti-mouse" antibodies which, in clinical trials, have been shown to neutralize the activity of mouse monoclonal antibodies. The use of our human monoclonal antibodies can circumvent these difficulties.

Another apparent difference between human and mouse monoclonal antibodies is their patterns of labeling. Previous studies with mouse antibodies have demonstrated that there is often a heterogenous labeling of cells within tumor sections. This pattern of reactivity has been attributed by some authors to antigenic heterogeneity of tumor cells (Hand et al., *Cancer Research*, 43:728–735, 1983). In contrast, the human monoclonal antibodies developed by our strategy were homogeneous in terms of their reactivity with tumors to which they did react. A plausible explanation for the heterogenous staining of mouse monoclonal antibodies is that it is a reflection of the murine immune recognition of phase- or cell-cycle-specific differentiation antigens abundant on the tumor cells rather than putative tumor associated antigens. It is not unreasonable to expect that when one immunizes mice with human tumor cells there would be substantial antigenic competition resulting in the more abundant and more predominant tissue-type and differentiation antigens successfully competing with relatively minor tumor associated antigens for immune responsiveness by the host. Thus, autologous immunization of man may result in the elicitation of antibodies against the group of antigens normally poorly immunogenic in mice. This evidence suggests that humans and mice may respond to different tumor antigens. In concert with this hypothesis is our finding that none of the first 36 human monoclonal antibodies we produced appeared to react with carcinoembryonic antigen (CEA), an antigen frequently recognized by murine monoclonal antibodies made against human tumor cells.

The majority of past attempts to develop human monoclonal antibodies have used B-cells extracted from either peripheral blood or lymph nodes from patients bearing tumors. It was believed that the presence of the antigenic tumor would cause a tumor-bearing individual to mount an immune response against his tumor and produce specifically immune B-cells. Thus, B-cells were taken from lymph nodes draining tumors in cancer patients or from circulating lymphocytes found in peripheral blood. However, prior to the present invention, there has been limited success in creating tumor- specific monoclonal antibodies.

The major problem in creating monoclonal antibodies specific for human tumor antigens has been the inability to find a source of specifically immune B-cells (Science, 1982, 216:285). In humans, the initial foci of cancer cells tend to grow over long periods of time, from 1% to 10% of the human lifespan, before there is any palpable clinical evidence of the disease. By this time patients are immunologically hyporesponsive to their tumors, or possibly immunologically tolerant. Thus, prior to the present invention, human monoclonal antibodies reactive with tumor cells could not reproducibly be obtained. Furthermore, of the small number of human monoclonal antibodies obtained from cancer patients, very few reacted with determinants found on the surface of tumor cells, but rather with intracellular determinants (R. J. Cote et al, PNAS, 1983, 80:2026). The present invention permits the development of monoclonal antibodies reactive with surface antigens; a requisite activity for tumor imaging and therapy.

SUMMARY OF THE INVENTION

81AV78 is a human monoclonal antibody isotyped in an ELISA assay as class IgM. In this assay, reactivity was seen with polyclonal goat antiserum to human IgM but no reactivity with antiserum to human IgG, IgA or mouse immunoglobulins IgG or IgM. SDS-Page analysis of purified 81AV78 indicated an 80 Kd heavy chain and 25 Kd light chain structure appropriate for human IgM.

DETAILED DESCRIPTION OF THE INVENTION

This invention is, specifically, a human diploid cell line, an immortalized human B-cell line transformed by exposure to EBV, designated as 81AV78. It produces a human IgM antibody specifically reactive with a colon tumor antigen CTAA 81AV78 described in application Ser. No. 07/701,752, now abandoned, CTAA 81AV78, THE ANTIGEN RECOGNIZED BY HUMAN MONOCLONAL ANTIBODY 81AV78, by Nicholas Pomato and Janet H. Ransom, filed coincidentally herewith, which is included herein by reference. CTAA 81AV78 is phosphorylated, nonglycoscylated lipid antigen found in colon carcinoma tumor tissue and on tumor cell lines.

We have successfully digested solid human malignancies using various enzyme preparations, The tumor dissociations were evaluated for yield of tumor cells per gram of tissue, cell types recovered, cell viability, cell size, and sterility. The criteria for successful vaccines for active specific immunotherapy are shown in Table 1.

The tumor tissue was surgically removed from a patient with metastatic colon carcinoma, separated from any non-tumor tissue, and cut into small pieces. The tumor fragments were then digested to free individual tumor cells by incubation in an enzyme solution.

After digestion, the freed cells were pooled and counted, and cell viability was assessed. The trypan blue exclusion test was found to be an acceptable measure of cell viability. The tumor cells were then cryopreserved and stored in liquid nitrogen.

The vaccine was prepared for injection by rapidly thawing cryopreserved cells, diluting the cells, washing with HBSS, resuspending, counting, and assessing viability.

Viable tumor cells were irradiated to render them nontumorigenic. The volume of the cell suspension in HBSS was adjusted such that $10^7$ viable cells remained in the tube. The cells were centrifuged, the supernatant was removed, and $10^7$ viable BCG were added in a volume of 0.1 ml. Hank's Balanced Salt Solution (HBSS) was added in sufficient quantity for a final volume of 0.2 ml. A third vaccine was similarly prepared, omitting the BCG.

The patient was immunized by intradermal inoculation with the tumor cell vaccine. $10^7$ viable tumor cells admixed with BCG were used for the first two vaccinations and $10^7$ tumor cells alone were used for the third vaccination. Scheduling each vaccination one week apart was found to be a successful procedure for inducing antibody production by the patient's peripheral blood lymphocytes.

Venous blood was collected from the immunized patient one week after each vaccination. Peripheral blood lymphocytes (PBLs) were separated from the collected blood for transformation.

Transformed human B-cells (diploid cells) that produced tumorspecific antibodies were prepared. B-cells were incubated with EBV for a period of time to let the virus be adsorbed, after which the cells were separated by the EBV containing medium, resuspended, and screened. The transformed B-cells were pre-screened for synthesis of human immunoglobulin and then tested on tissues for specificity to tumor associated antigens. Thus, well supernatants that tested positively for reactions with tumor tissue and negatively for reactions with normal tissue and with CEA contained transformed B-cells.

Example I: Preparation of Sensitized B-Cells

A. Patient Selection.

Patients undergoing surgical resection of colon or rectal cancers were selected for a randomized trial of active specific immunotherapy. Randomization was done with stratification according to pathologic stage and tumor was obtained from all patients who met the clinical criteria. Candidates for the study were colorectal cancer patients with no previous history of cancer, who had received no prior chemotherapy or radiation therapy, and who were in suitable medical condition to comply with the outpatient treatment protocol. Patients eligible for the trial were those with tumor extending through the bowel wall (Astler-Coller B2), positive lymph nodes (stages C1, C2) or patients with metastatic disease (stage D). Within these classifications, patients were randomly selected for participation in treatment and non-treatment groups. Randomization cards were computer generated and sequentially drawn from each category postoperatively.

B. Tumor Acquisition

After surgical resection the bowel specimen was taken immediately to the hospital pathology department and opened under sterile conditions. Tumor tissue was excised, placed in sterile tubes containing Hank's Balanced Salt Solution (HBSS) containing 50 μg gentamicin per ml and carried immediately on ice to the laboratory for processing and freezing.

C. Dissociation of Solid Tumor and Colon Mucosa

The tissue dissociation procedure of Peters et al (*Cancer Research*, 39:1353–1360, 1979) was employed using sterile techniques throughout under a laminar flow hood. Tumor tissue was rinsed three times in the centrifuge tube with HBSS and gentamicin and transferred to a petri dish on ice. Scalpel dissection removed extraneous tissue and the tumor was minced into pieces approximately 2 to 3 mm in diameter. Tissue fragments were placed in a 75 ml flask with 20–40 ml of 0.14% (200 units/ml) Collagenase Type 1 (Sigma C—0130) and 0.1% (500 Kunitz units/ml) deoxyribonuclease type 1 (Sigma D—0876) (DNAase 1, Sigma D-0876) prewarmed to 37° C. Flasks were placed in a 37° C. waterbath with submersible magnetic stirrers at a speed which caused tumbling, but not foaming. After a 30-minute incubation free cells were decanted through three layers of sterile medium-wet nylon mesh (166t: Martin Supply Co., Baltimore, Md.) into a 50 ml centrifuge tube. The cells were centrifuged at 1200 rpm (250×g) in a refrigerated centrifuge for 10 minutes. The supernatant was poured off and the cells were resuspended in 5–10 ml of DNAase (0.1% in HBSS) and held at 37° C. for 5–10 minutes. The tube was filled with HBSS, washed by centrifugation, resuspended to 15 ml in HBSS and held on ice. The procedure was repeated until sufficient cells were obtained, usually three times for tumor cells. Cells from the different digests were then pooled, counted, and cell viability assessed by the trypan blue exclusion test. The cells were centrifuged for a final wash prior to cryopreservation.

D. Cryopreservation

Optimal cryopreservation was a primary concern. For vaccine preparation, the dissociated tumor cells were adjusted to $5-8\times 10^7$/ml in HBSS and added in equal volume to chilled 2×freezing medium containing 15% dimethylsulfoxide (DMSO) and 4% human serum albumin (HSA). The final suspension of 2 to $4\times 10^7$ cells/ml were placed in 1.2 ml Nunc freezer vials. For DCH cell testing the procedure was the same except that no HSA was used. In both cases, in preparation for freezing, the Nunc vials were transferred on ice to a Cryo-Med model 990 Biological Freezer with a model 700 Controller and a model 500 Temperature Recorder for controlled-rate freezing. Care was taken that the temperature of the individual vials, including the monitor vial, was uniform at the beginning of the freezing process. Vials were cooled at a controlled rate of $-1°$ C./min to a final temperature of $-80°$ C. The vials were transferred in liquid nitrogen to liquid nitrogen storage.

E. Clinical Protocol

Patients with tumors of the appropriate pathologic stages were randomized to receive either the autologous tumor cell-BCG vaccine or to have no further therapy. The stage D patients all received 5-fluorouracil chemotherapy and all patients with lesions below the peritoneal reflection (rectal cancer) received 5040 rads of pelvic X-irradiation two weeks after immunotherapy was completed. The vaccines were started at 4–5 weeks after tumor resection to allow sufficient time for recovery of immunologic suppression induced by anesthesia and surgery. At 3–4 weeks after resection both control and treatment patients were skin tested with standard recall antigens as well as graded doses of their autologous tumor cells. Recall antigens used were: Mumps skin test antigen, USP, Eli Lilly, Indianapolis, Ind.; Aplisol, PPD, (Tuberculin Purified Protein Derivative), Parke-Davis, Detroit, Mich.; Trichophyton, diluted 1:30, Center Laboratories, Port Washington, N.Y.; and Candida albicans diluted 1:100, Center Laboratories, Port Washington, N.Y., 0.1 ml of each was placed intradermally on the forearm and examined for erythema and induration at 24 and 48 hours.

Patients selected for treatment protocol received 3 weekly intradermal vaccine injections consisting of $10^7$ irradiated, autologous tumor cells and $10^7$ BCG in the first 2 vaccines with $10^7$ tumor cells alone in the final. Fresh-frozen Tice BCG, supplied by University of Illinois, Chicago, Ill., was stored at $-70°$ C. The first vaccine was placed on the left anterior thigh approximately 10 cm below the groin crease, the second in a comparable location on the right thigh and the third in the right deltoid area.

F. Preparation of Vaccine

On the day of the first and second vaccinations, the vial was rapidly thawed in a 37° C. waterbath, tumor cells were diluted slowly to 15 ml in HBSS, washed once by centrifugation at 1200 rpm and resuspended to 15 ml in HBSS. Cell counts and viability determinations were made using the trypan blue exclusion test. Viability ranged between 70 and 90%, with a mean of 80%. The cells were washed once by centrifugation at 1200 rpm and resuspended to 15 ml in HBSS. The suspension of tumor cells was placed on ice and irradiated at 4020 rads/min for a total of 20,000 rads. The volume of the cell suspension was adjusted such that $10^7$ viable tumor cells remained in the tube ($1.3\times 10^7$ viable cells are included to allow for cell loss in tubes and syringes, and for the possibility of approximately 20% misidentification of lymphoid cells). The cells were centrifuged, the supernatant removed and $10^7$ BCG were added in a volume of 0.1 ml. HBSS was added in sufficient quantity for a final volume of 0.2 ml. The third vaccine was similarly prepared, omitting the BCG.

G. Results of Immunization

Reactivity to Standard Recall Antigens

All patients were reactive initially to at least one of the standard recall antigens. Two of the 29 were reactive to candida, 26 of 29 were reactive to mumps, 16 of 29 were reactive to PPD and 3 of 29 reacted to trichophyton. There was no significant change in reactivity in the follow-up period except that all but two of the immunized patients converted to PPD positivity.

H. Delayed Cutaneous Hypersensitivity (DCH) to Tumor Cells

Four of 24 patients (17%) had a positive DCH to $10^6$ tumor cells prior to the course of immunization. This was not significantly different from the one of 11 patients (9%) testing positive in the non-immunized control group. Of significance ($p < 0.1$) all of the initially four positive responders and 12 of the negative responders in the immunization group boosted to greater DCH reactivity following a course of immunotherapy (67% became positive). Seven of these patients have been tested at one year, with three maintaining a positive response. Only three of the 16 objectively immunized patients demonstrated a positive DCH response to $10^5$ tumor cells at 6 weeks, with none showing a response to $10^4$ cells.

Example II: Production of Cells Producing Human Monoclonal Antibodies

A. Removal and Processing of Immunized B-Cells from Patients

Patients were bled at the time of the second immunization, one week after the first immunization, and at the time of the third vaccination, one week after the second immunization. Venous blood was collected aseptically in the presence of preservative-free heparin (O'Neill, Jones and Feldman, St. Louis, Mo.) at a final concentration of 17 units/ml. The blood was maintained at room temperature and transported to the laboratory expeditiously, within a few hours of collection.

The blood, diluted 1:2 with calcium and magnesium-free HBSS, was layered (4 ml) over 3 ml of lymphocyte separation medium (LSM, Litton Bionetics) and centrifuged in a 15 ml centrifuge tube for 30 minutes at $400\times g$. The cells at the interface were removed, diluted with three times their volume of HBSS and pelleted (1000 rpm for 10 minutes). The peripheral blood lymphocytes were resuspended in 10 ml of serum-free Hepes-buffered Dulbecco's MEM (DMEM), counted and viability determined.

An alternative method was also used to recover immunized B-cells. The T-lymphocytes were removed by resetting with AET-treated sheep erythrocytes. Sheep erythrocytes (in Alsever's solution) were washed three times with balanced salt solution (BSS) and incubated at 37° C. for 20 minutes with four times the packed cell volume with 0.14 M AET (Sigma). The treated cells were then washed three times with HBSS and resuspended to a 10% suspension. The treated erythrocytes were layered over LSM, centrifuged at 2500 rpm and the pellet collected. Following three washes with HBSS, the sheep erythrocytes were resuspended to a 10% suspension in undiluted fetal bovine serum and used within two weeks. The PBLs (up to 80 million cells) were mixed with 1 ml of AET-treated sheep erythrocytes and pelleted at 1000 rpm for 10 minutes at 4° C. The pellet was incubated on ice for 45 minutes, gently resuspended with a wide bore pipette and layered over 3 ml LSM. The rosetted cells were centrifuged at $400\times g$ for 40 minutes at room temperature. The T-cell depleted PBLs were collected at the interface, washed with three times the volume HBSS, and pelleted. Following counting and viability determination, the PBLs enriched for B-cells were then used for hybridoma generation.

B. EBV Transformation Procedure

Peripheral blood B-cells from immunized patients were exposed to transforming agents, resulting in continuously growing cell lines that produce monoclonal antibodies. We used EBV as the transforming agent, although any effective lymphotropic virus or other transforming agent able to transform the B-cells to grow in continuous culture and still produce monoclonal antibodies specific for tumor associated antigens can be used.

By our method, heparinized blood was separated on an LSM gradient and the mononuclear cell fraction was collected at the interface. The mononuclear cell fraction can either be used at this point or cryopreserved for future transformation.

Prior to transformation, in some instances, we depleted the mononuclear cell fraction of macrophages and other cells that might inhibit transformation. Two techniques used were plastic adherence and treatment with the methyl ester of L-leucine. In the plastic adherence technique, the cells were suspended in cell culture medium (RPMI 1640 medium, Gibco, Grand Island, N.Y.) containing 20% fetal bovine serum ($2\times 10^6$/ml) and incubated overnight in plastic cell culture dishes. Non-adherent cells were removed from the plastic by pipetting, leaving the lymphocytes. Alternatively, the cells were incubated in methyl ester L-leucine (5 mM in serum-free cell culture medium) for 40 minutes at room temperature and then washed.

The lymphocytes, either fresh or cryopreserved, either unfractionated or depleted of some non-B cells, were counted and between 2 and $5\times 10^6$ cells were pelleted. The pelleted cells were resuspended in 5 ml of freshly harvested Epstein Barr Virus in the form of undiluted B95-8 supernatant fluid harvested from a 4–6 day old culture of B95-8 cells, clarified by centrifugation at 2,000 rpm for 15 minutes at 4° C. and filtered through a 0.8 micron filter to insure that all cells had been removed. The B95-8 cell line was obtained from Dr. G. Tostado, Division of Biologics, FDA. The cells and EBV were incubated at 37° C. for 90 minutes for virus adsorption. During virus adsorption, the cells were agitated periodically.

After virus adsorption the cells were pelleted at room temperature, resuspended in cell culture medium containing 20% fetal bovine serum and counted. The cells were then diluted to about $5\times 10^4$ cells/ml and approximately 100 µl plated into each well of a 96 well plate. An additional 100 µl of cell culture medium was then added to each well. Alternatively, the cells may be plated into wells containing irradiated feeder cells (such as J774). The mouse macrophage line J774 (ATCC, Rockville, Md.) were irradiated (20,000 rads) and then cryopreserved. The cells were thawed and then plated ($5 \times 10^3$ cells/well) into 96 well plates one day before the EBV transformation were to be seeded.

The cell culture media was changed twice per week for up to 6–8 weeks. Screening of supernatant fluid from wells exhibiting extensive cell growth to select those synthesizing human immunoglobulin and the culturing of selected cell lines was performed for selection and culturing of monoclonal antibody producing cells.

C. Screening of Diploid Cells

EBV transformed cells were quantified and isotyped by a capture enzyme-linked immunoassay (ELISA) for the synthesis of human immunoglobulin (IgA, IgG and IgM). The standard Bio-EnzaBead method was utilized, which is sensitive in the range of 10–300 ng/ml. The hybridoma supernatant fluids were diluted 1:30 with an effective range of 0.3–9 µg/ml. Only cells that synthesized human immunoglobulin at a concentration of greater than or equal to 1 µg/ml were tested by indirect immunoperoxidase on tissues after the isotype of the antibody (IgA, IgG or IgM) was determined.

Polycarbonate-coated metallic beads (Bio-EnzaBead$^{TM}$, Litton Bionetics) were incubated with goat antibodies to human immunoglobulins (IgG+IgA+IgM) overnight at 4° C. and then blocked (30 min at room temperature) with 2.5% BSA to prevent non-specific binding. The beads were then air dried and stored at 4° C. The ELISA for detection of immunoglobulin was performed as follows. Supernatant fluid from a 96-well culture plate was diluted, incubated with the antibody-capture bead for 1 hr at 37° C., washed, and then incubated for 1 hr at 37° C. with peroxidase-labeled affinity-purified goat antibody to human immunoglobulins (IgG+IgA IgM). The washed beads were then incubated (10 min at room temperature) with 2,2'-Azino-di[3-ethyl-benzthiazoline-6-sulfonic acid], and the optical density was determined at 405 nm. The immunoglobulin concentrations were interpolated mathematically from the linear portion of a standard curve (30–1000 ng/ml) of human gamma globulin. Supernatant fluids containing >1 µg/ml were then isotyped using this ELISA with peroxidase-labeled goat antibodies to human $\gamma$, $\alpha$, and $\mu$ chains. Subsequent quantitative assays used an immunoglobulin standard appropriate for the monoclonal antibody isotype. Mouse immunoglobulins were assayed with Bio-EnzaBeads coated with goat antimouse IgG+IgM (H+L) and peroxidaseconjugated goat antimouse IgG+IgM (H+L). In other experiments, supernatant fluids were incubated with the anti-human Ig beads and the peroxidase-conjugated goat antimouse IgG+IgM (H+L).

Cryostat sections of normal and tumor tissue, stored at −30° C., were post-fixed in PLP (0.5% p-formaldehyde, 0.075M L-lysine, 0.01 M sodium periodate) for 20 minutes at 4° C. The sections were then washed. Paraffin sections of 10% formalin-fixed tissues were deparaffinized immediately before use. The cryostat and paraffin sections were then incubated at room temperature in 1% bovine serum albumin in PBS containing 0.075 M L-lysine for 20 minutes. The sections were incubated overnight at 4° C. with supernatant fluids. Following three washes with PBS, the sections were then incubated with the appropriate anti-human peroxidase-labeled reagent for 60 minutes at 37° C., washed and incubated at room temperature for 15 minutes with diaminobenzidine (0.5 mg/ml, Ph 7.6) in PBS containing 0.1% hydrogen peroxide. The sections were washed with PBS, stained with hematoxylin, dehydrated, and mounted with permount.

These methods permitted the widest spectrum of tissue reactive antibodies to be detected (i.e., directed against surface or cytoplasmic antigens).

To isolate broadly reactive antibodies, the supernatant fluids were screened against a panel of tumor sections. Cell lines producing monoclonal antibodies were then cloned by limiting dilution.

D. Production of Monoclonal Antibodies

Human monoclonal antibody producing cells were grown in RPMI 1640 medium (Gibco, Grand Island, New York) supplemented with 10% fetal bovine serum, 3 Mm L-glutamine and 5 µg/ml gentamicin. The cells were at 37° C. (35°–38° C.) under a humidified atmosphere of 7.5% $CO_2$ in air. The antibody was harvested from the highly metabolized spent medium by pelletizing the medium free of cells (e.g., by centrifuging at 500 rpm for 15 minutes).

Example III: Reactivity of Monoclonal Antibodies to Normal and Tumor Tissue

Most of the antibodies exhibited substantially reduced binding to normal colonic mucosa. The antibodies reactive with paraffin sections Were also tested for reactivity with normal tissue. 81AV78 showed negative reactivity with the following normal human tissues: ovary, uterus, cervix, testes, adrenal glands, thyroid, thymus, lymph nodes, spleen, bone marrow, myocardium, brain, spinal cord, skin, muscle and hemopoietic cells. 81AV78 exhibited slight reactivity with the following tissues: colon (border and superficial glands), small intestine (border and superficial glands), stomach (gastric pits and superficial glands), esophagus (basal layer of squamous epithelial cells and glands), pancreas (some ductal epithelium), kidney (20–50% of collecting tubules), breast (gland and ductal epithelium), lung (some alveolar ducts), and liver (ducts (3/5 specimens were positive)). Reactivity of 81AV78 with human tumor cell lines is shown in Table 2. Tables 3 and 4 show the reactivity of 81AV78 with tumor tissue specimens.

Techniques including the preparation of protein extracts and the use of immunoadsorbent lectins for the immunization of mice are required to produce monoclonal antibodies against protein antigens derived from colon tumors. Thus, autologous immunization of man elicits antibodies against a group of antigens normally poorly immunogenic for mice. It is therefore possible that man and mice may respond to different tumor-associated antigens. In concert with this hypothesis is the finding that none of 28 different monoclonal antibodies prepared by this method that we examined reacted with purified CEA, an antigen frequently seen by murine monoclonal antibodies made against colon tumor cells, (Koprowski et al, *Somat. Cell Genet.,* 5:957–972, 1979.

In addition to providing monoclonal antibodies reactive with tumor cell surface antigens for the in vivo diagnosis and immunotherapy of cancer, the invention provides monoclonal antibodies useful as probes to isolate and characterize the antigens relevant to human cancer immunity. The antigen identified by 81AV78 is likely to be useful as a tumor vaccine, as indicated by a positive response in T-cell proliferation assays. In addition, the generation of antibody producing diploid cells adds a dimension of genetic stability to the production of human monoclonal antibodies reactive with tumor cell surface antigens.

The cell line producing the IgM human monoclonal antibody 81AV78 was deposited with the American Type Culture Collection, 12301 Parklawn Drive, Rockville, Md. 20852, USA, on May 16, 1991. The cell line deposited is identified as follows: The antigen identified by 81AV78 may also be targeted by the antigen binding portion of the 81AV78 antibody. It is well known that variable region fragments can be used in place of the complete antibody for some purposes. Such portions of the antibody, which we term antigen binding units, comprise the variable region antigen binding portion of 81AV78 and may be derived by enzymatically cleaving the antibody, by sequencing the antibody and then synthesizing by conventional peptide synthesis means or by expression of the antigen binding portion of the antibody through recombinant means using that portion of the nucleic acid sequence coding for the variable region.

| Identification | Accession Number |
|---|---|
| Human B-Cell Derived Cell Line, 81AV78 | ChL 10750 |

TABLE 1

CRITERIA FOR SUCCESSFUL VACCINES FOR ACTIVE SPECIFIC IMMUNOTHERAPY

Adjuvant
(a) BCG (Phipps, Tice, Connaught); Lyophilized, frozen (dose-dependence >$10^6$ ($10^7$–$10^8$))
(b) C. parvum (Wellcome Labs) (dose-dependence >7 μg (70 μg–700 μg)
Tumor Cells
(a) Enzymatic dissociation
   (1) Collagenase type I (1.5–2.0 U/ml HBSS)
   (2) DNAase (450 D.U./ml HBSS)
   (3) 37° C. with stirring
(b) Cryopreservation
   (1) Controlled-rate freezing (−1° C./min) (7.5% DMSO, 5% HSA, HBSS)
   (2) Viability 80%
(c) X-irradiation
   (1) Rendered non-tumorigenic at 12,000–20,000 R.
Components and Administration[1]
(a) Ratio of adjuvant to tumor cells - 10:1–1:1 (optimum)
(b) $10^7$ tumor cells (optimum)
(c) 2–3 i.d. vaccinations at weekly intervals. Third vaccination contains tumor cells only.

[1]Isoniazid chemoprophylaxis of BCG infection optional.
BCG - Bacillus Calmette Guerin
HBSS - Hanks' Balanced saline solution
DMSO - Dimethylsulfoxide
HSA - Human serum albumin
R - Rads
PBS - Phosphate buffered saline
EDTA - Ethylenediaminetetraacetic acid

TABLE 2

REACTIVITY OF HUMAN MONOCLONAL ANTIBODY 81AV78
Indirect Immunofluorescence with Live Tumor Cells[a,d]

| Cell Line | Tumor Type | Fluorescence Intensity[a] |
|---|---|---|
| Ht-29 | Colon Carcinoma | 2+[b] (100%)[c] |
| SKCO-1 | Colon Carcinoma | 3+ (70%) |
| WiDr | Colon Carcinoma | − |
| HCT-8 | Colon Carcinoma | 3+ (60%) |
| Bt-20 | Breast Carcinoma | − |
| EP | Breast Carcinoma | 3+ (50%) |
| MCF-7 | Breast Carcinoma | − |
| CaLu-1 | Lung Adenocarcinoma | 2+ (75%) |
| A2780 | Ovarian Carcinoma | − |
| Ovcar3 | Ovarian Carcinoma | 2+ (50%) |
| Panc-1 | Pancreatic Carcinoma | 2+ (60%) |
| WI-38 | Normal Fibroblasts | − |

[a]Concentration of 81AV78 is 10 μg/ml. Reactivity with a control human IgM at 10 μg is negative on all cells.
[b]Florescence Intensity: 4+ strong, 3+ moderate, 2+ weak to moderate, 1+ weak, − negative.
[c]Percentage of cells showing the indicated fluorescence intensity. Remainder of cells are not fluorescent.
[d]Staining of acetone fixed permeabilized cells shows a filamentous cytoskeletal staining pattern. All cell lines give strong fluorescence staining with acetone fixed cells.

TABLE 3

REACTIVITY OF HUMAN MONOCLONAL ANTIBODY 81AV78
Indirect Immunohistochemical Studies with Human Colon Carcinoma Xenografts

| Tumor | Differentiation | 81AV78 5.0 μg/ml | 81AV78 2.5 μg/ml | Control IgM 5.0 μg/ml |
|---|---|---|---|---|
| EPP | Poorly differentiated | 4+[a] | 3+ | − |
| ATK | Poorly differentiated | 4+ (50%)[b] | 3+ (50%) | − |
| ROB | Poor-Mod. Differentiated | 3+ | 3+ | − |
| SEI | Poor-Mod. Differentiated | 3+ | 2+ | − |
| HAW | Poor-Mod. Differentiated | 2+ (50%) | 1+ (50%) | − |
| NEK | Mod-Well Differentiated | 4+ | 3+ | − |
| KRE | Mod-well Differentiated | 1+ (50%) | − | − |
| BLU | Mod-Well Differentiated | 4+ | 4+ | − |
| BOM | Well Differentiated | 4+ | 3+ | − |
| WOR | Well Differentiated | 4+ | 3+ | − |
| JEF | Well Differentiated | 4+ | 4+ | − |
| THO | Well Differentiated | 4+ | 4+ | − |

[a]Staining intensity: 4+ strong, 3+ moderate, 2+ weak to moderate, 1+ weak, − negative.
[b]Percentage of cells stained. The proportion of cells recognized by the antibody is greater than 80% unless otherwise indicated.
Cell lines available from American Type Culture Collection, Rockville, Maryland.

TABLE 4

REACTIVITY OF HUMAN MONOCLONAL ANTIBODY 81AV78
Direct Immunohistochemical Studies with Fresh Frozen Colon Tumors

| Patient | Difference[a] | Biotin-labeled 81AV78 conc μg/ml 10 | 5.0 | 1.25 |
|---|---|---|---|---|
| 1 | | 4+[b,c] | 3+ | 1+ |
| 2 | | 2+ | 1+ | NT[d] |
| 3 | | 4+ | 4+ | 2+ |
| 4 | | 3+ | 2+ | − |
| 5 | | 3+ | 3+ | − |
| 6 | | 3+ | 2+ | 1+ |
| 12 | Poor | 3+ 75% | 3+ 75% | 1+ 20% |
| 13 | Mod | 3+ 20% | 3+ 10% | − |
| 14 | Poor | 2+ 50% | 1+ 10% | − |
| 15 | Mod-Well | 3+ 25% | 3+ 20% | − |
| 16 | Mod | 3+ 75% | 3+ 50% | 2+ 30% |
| 17 | Mod-Well | 4+ 90% | 4+ 80% | 3+ 50% |
| 18 | Poor | 3+ 10% | 3+ 10% | − |
| 19 | Poor-Mod | 4+ 80% | 4+ 80% | 2+ 80% |
| 20 | Well | − | − | − |
| 21 | Poor | − | − | − |

[a]Degree of differentiation.
[b]Intensity of staining: 4+ strong, 3+ moderate, 2+ weak to moderate, 1+ weak, − negative. Percentage of cells showing indicated level of staining. studies with a biotinylated human IgG gave negative staining at all concentrations at or below 10 μg/ml.
[c]Staining is cytoplasmic and only on epithelium. No nuclear staining. Endothelium, smooth muscle, fibroblasts, stroma and inflammatory cells are not stained.
[d]NT - not tested.

We claim:
1. Transformed human B-cell line 81AV78, having ATCC accession number CRL 10750.
2. Monoclonal antibody produced by a cell according to claim 1.

* * * * *